(12) United States Patent
Henkes et al.

(10) Patent No.: US 11,426,293 B2
(45) Date of Patent: *Aug. 30, 2022

(54) MEDICAL IMPLANT

(71) Applicant: USSC Medical GmbH, Meerbusch (DE)

(72) Inventors: Hans Henkes, Essem (DE); Achim Flesser, Mettmann (DE); Ronald Kontek, Herne (DE); Jürgen Speder, Bochum (DE); Ralph Bodenburg, Bochum (DE)

(73) Assignee: USSC MEDICAL GMBH, Meerbusch (DE)

( * ) Notice: Subject to any disclaimer, the term of this patent is extended or adjusted under 35 U.S.C. 154(b) by 148 days.

This patent is subject to a terminal disclaimer.

(21) Appl. No.: 16/420,814

(22) Filed: May 23, 2019

(65) Prior Publication Data
US 2019/0307585 A1 Oct. 10, 2019

Related U.S. Application Data

(63) Continuation of application No. 14/136,281, filed on Dec. 20, 2013, now Pat. No. 10,342,683, which is a
(Continued)

(30) Foreign Application Priority Data

Jul. 19, 2002 (DE) .................................. 10233085.9

(51) Int. Cl.
*A61F 2/82* (2013.01)
*A61F 2/92* (2013.01)
(Continued)

(52) U.S. Cl.
CPC .......... *A61F 2/82* (2013.01); *A61B 17/12118* (2013.01); *A61B 17/221* (2013.01);
(Continued)

(58) Field of Classification Search
CPC .......... A61F 2/24; A61F 2/2427; A61F 2/243; A61F 2/2436; A61F 2/2439; A61F 2/95;
(Continued)

(56) References Cited

U.S. PATENT DOCUMENTS 3,996,938 A 12/1976 Clark, III
4,046,150 A 9/1977 Schwartz et al.
(Continued)

FOREIGN PATENT DOCUMENTS

BR 9604566-3 9/1998
CA 2389374 5/2001
(Continued)

OTHER PUBLICATIONS

European Search Report dated Jan. 21, 2016; European Patent Application No. 15190138.6; 2 pages.
(Continued)

*Primary Examiner* — Marcia L Watkins
(74) *Attorney, Agent, or Firm* — Fortem IP LLP; Matthew Lincicum

(57) ABSTRACT

A medical having a proximal and a distal end, that is preformed to assume a superimposed structure at an implantation site but can be made to take on a volume-reduced form making it possible to introduce it by means of a microcatheter and a guide wire arranged at the proximal end, with the implant in its superimposed structure assuming the form of a longitudinally open tube and having a mesh structure of interconnected strings or filaments. The implant has a tapering structure at its proximal end where the strings or filaments converge at a connection point.

21 Claims, 6 Drawing Sheets

Related U.S. Application Data continuation of application No. 11/935,252, filed on Nov. 5, 2007, now Pat. No. 8,632,584, which is a continuation of application No. 11/039,066, filed on Jan. 19, 2005, now Pat. No. 7,300,458, which is a continuation of application No. PCT/EP03/07926, filed on Jul. 21, 2003.

(51) Int. Cl.
| | | |
|---|---|---|
| *A61F 2/95* | (2013.01) | |
| *A61B 17/12* | (2006.01) | |
| *A61B 17/221* | (2006.01) | |
| *A61F 2/91* | (2013.01) | |
| *A61F 2/915* | (2013.01) | |
| *A61F 2/966* | (2013.01) | |
| *A61F 2/30* | (2006.01) | |

(52) U.S. Cl.
CPC .............. *A61F 2/91* (2013.01); *A61F 2/915* (2013.01); *A61F 2/92* (2013.01); *A61F 2/95* (2013.01); *A61F 2/966* (2013.01); *A61B 2017/12063* (2013.01); *A61B 2017/2215* (2013.01); *A61F 2002/3008* (2013.01); *A61F 2002/91525* (2013.01); *A61F 2002/91541* (2013.01); *A61F 2002/91558* (2013.01); *A61F 2002/9528* (2013.01); *A61F 2002/9534* (2013.01); *A61F 2220/005* (2013.01); *A61F 2220/0058* (2013.01); *A61F 2230/0008* (2013.01); *A61F 2250/0098* (2013.01)

(58) Field of Classification Search
CPC .... A61F 2/92; A61F 2/966; A61F 2002/9534; A61F 2002/9528
See application file for complete search history.

(56) References Cited

U.S. PATENT DOCUMENTS

| | | |
|---|---|---|
| 4,299,255 A | 11/1981 | Miller |
| 4,347,846 A | 9/1982 | Dormia |
| 4,403,612 A | 9/1983 | Fogarty |
| 4,611,594 A | 9/1986 | Grayhack et al. |
| 4,612,931 A | 9/1986 | Dormia |
| 4,650,466 A | 3/1987 | Luther |
| 4,655,771 A | 4/1987 | Wallsten |
| 4,733,665 A | 3/1988 | Palmaz |
| 4,739,762 A | 4/1988 | Palmaz |
| 4,793,348 A | 12/1988 | Palmaz |
| 4,820,298 A | 4/1989 | Leveen et al. |
| 4,890,611 A | 1/1990 | Monfort et al. |
| 5,064,435 A | 11/1991 | Porter |
| 5,071,407 A | 12/1991 | Termin et al. |
| 5,100,423 A | 3/1992 | Fearnot |
| 5,102,417 A | 4/1992 | Palmaz |
| 5,190,058 A | 3/1993 | Jones et al. |
| 5,192,286 A | 3/1993 | Phan et al. |
| 5,195,984 A | 3/1993 | Schatz |
| 5,197,978 A | 3/1993 | Hess |
| 5,217,484 A | 6/1993 | Marks |
| 5,222,971 A | 6/1993 | Willard et al. |
| 5,330,482 A | 7/1994 | Gibbs et al. |
| 5,354,295 A | 10/1994 | Guglielmi et al. |
| 5,411,549 A | 5/1995 | Peters |
| 5,423,829 A | 6/1995 | Pham et al. |
| 5,456,667 A | 10/1995 | Ham et al. |
| 5,490,859 A | 2/1996 | Mische et al. |
| 5,496,330 A | 3/1996 | Bates et al. |
| 5,501,694 A | 3/1996 | Ressemann et al. |
| 5,527,326 A | 6/1996 | Hermann et al. |
| 5,540,680 A | 7/1996 | Guglielmi et al. |
| 5,540,707 A | 7/1996 | Ressemann et al. |
| 5,569,245 A | 10/1996 | Guglielmi et al. |
| 5,571,122 A | 11/1996 | Kelly et al. |
| 5,573,520 A | 11/1996 | Schwartz et al. |
| 5,624,449 A | 4/1997 | Pham et al. |
| 5,669,933 A | 9/1997 | Simon et al. |
| 5,690,667 A | 11/1997 | Gia |
| 5,695,519 A | 12/1997 | Summers et al. |
| 5,720,764 A | 2/1998 | Naderlinger |
| 5,725,572 A | 3/1998 | Lam et al. |
| 5,743,905 A | 4/1998 | Eder et al. |
| 5,749,883 A | 5/1998 | Halpern |
| 5,759,192 A | 6/1998 | Saunders |
| 5,769,882 A | 6/1998 | Fogarty et al. |
| 5,792,145 A | 8/1998 | Bates et al. |
| 5,792,157 A | 8/1998 | Mische et al. |
| 5,800,454 A | 9/1998 | Jacobsen et al. |
| 5,800,519 A | 9/1998 | Sandock |
| 5,800,520 A | 9/1998 | Fogarty et al. |
| 5,800,525 A | 9/1998 | Bachinski et al. |
| 5,814,064 A | 9/1998 | Daniel et al. |
| 5,824,037 A | 10/1998 | Fogarty et al. |
| 5,827,304 A | 10/1998 | Hart |
| 5,836,868 A | 11/1998 | Ressemann et al. |
| 5,848,964 A | 12/1998 | Samuels |
| 5,851,206 A | 12/1998 | Guglielmi et al. |
| 5,855,578 A | 1/1999 | Guglielmi et al. |
| 5,882,329 A | 3/1999 | Patterson et al. |
| 5,891,128 A | 4/1999 | Gia et al. |
| 5,893,887 A | 4/1999 | Jayaraman |
| 5,895,385 A | 4/1999 | Guglielmi et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,717 A | 6/1999 | Jacobsen et al. |
| 5,911,734 A | 6/1999 | Tsugita et al. |
| 5,913,895 A | 6/1999 | Burpee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,061 A | 7/1999 | Ogi et al. |
| 5,928,226 A | 7/1999 | Guglielmi et al. |
| 5,935,139 A | 8/1999 | Bates |
| 5,941,869 A | 8/1999 | Patterson et al. |
| 5,944,714 A | 8/1999 | Guglielmi et al. |
| 5,947,962 A | 9/1999 | Guglielmi et al. |
| 5,947,995 A | 9/1999 | Samuels |
| 5,948,016 A | 9/1999 | Jang |
| 5,954,743 A | 9/1999 | Jang |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |
| 5,980,514 A | 11/1999 | Kupiecki et al. |
| 5,984,929 A | 11/1999 | Bashiri et al. |
| 6,010,498 A | 1/2000 | Guglielmi |
| 6,013,093 A | 1/2000 | Nott et al. |
| 6,039,721 A | 3/2000 | Johnson et al. |
| 6,063,100 A | 5/2000 | Diaz et al. |
| 6,063,111 A | 5/2000 | Hieshima et al. |
| 6,066,149 A | 5/2000 | Samson et al. |
| 6,066,158 A | 5/2000 | Engelson et al. |
| 6,077,260 A | 6/2000 | Wheelock et al. |
| 6,083,220 A | 7/2000 | Guglielmi et al. |
| 6,096,034 A | 8/2000 | Kupiecki et al. |
| 6,096,053 A | 8/2000 | Bates |
| 6,099,549 A | 8/2000 | Bosma et al. |
| 6,110,198 A | 8/2000 | Fogarty et al. |
| 6,118,001 A | 9/2000 | Owen et al. |
| 6,123,714 A | 9/2000 | Gia et al. |
| 6,129,755 A | 10/2000 | Mathis et al. |
| 6,146,396 A | 11/2000 | Konya et al. |
| 6,156,061 A | 12/2000 | Wallace et al. |
| 6,165,178 A | 12/2000 | Bashiri et al. |
| 6,165,213 A | 12/2000 | Goicoechea et al. |
| 6,168,592 B1 | 1/2001 | Kupiecki et al. |
| 6,168,603 B1 | 1/2001 | Leslie et al. |
| 6,179,857 B1 | 1/2001 | Diaz et al. |
| 6,187,017 B1 | 2/2001 | Gregory, Jr. |
| 6,190,394 B1 | 2/2001 | Lind et al. |
| 6,193,745 B1 | 2/2001 | Fogarty et al. |

(56) References Cited

U.S. PATENT DOCUMENTS

| | | |
|---|---|---|
| 6,203,552 B1 | 3/2001 | Bagley et al. |
| 6,214,025 B1 | 4/2001 | Thistle et al. |
| 6,238,412 B1 | 5/2001 | Dubrul et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,686 B1 | 7/2001 | Rieu et al. |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,306,141 B1 | 10/2001 | Jervis |
| 6,312,463 B1 | 11/2001 | Rourke et al. |
| 6,325,815 B1 | 12/2001 | Kusleika et al. |
| 6,336,934 B1 | 1/2002 | Gilson et al. |
| 6,344,041 B1 | 2/2002 | Kupiecki et al. |
| 6,361,558 B1 | 3/2002 | Hieshima et al. |
| 6,371,969 B1 | 4/2002 | Tsugita et al. |
| 6,379,329 B1 | 4/2002 | Naglreiter et al. |
| 6,383,205 B1 | 5/2002 | Samson et al. |
| 6,402,771 B1 | 6/2002 | Palmer et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,443,971 B1 | 9/2002 | Boylan et al. |
| 6,443,972 B1 | 9/2002 | Bosma et al. |
| 6,458,139 B1 | 10/2002 | Palmer et al. |
| 6,468,266 B1 | 10/2002 | Bashiri et al. |
| 6,485,524 B2 | 11/2002 | Strecker |
| 6,491,719 B1 | 12/2002 | Fogarty et al. |
| 6,500,182 B2 | 12/2002 | Foster |
| 6,514,273 B1 | 2/2003 | Voss et al. |
| 6,520,968 B2 | 2/2003 | Bates et al. |
| 6,530,935 B2 | 3/2003 | Wensel et al. |
| 6,533,811 B1 | 3/2003 | Ryan et al. |
| 6,551,342 B1 | 4/2003 | Shen et al. |
| 6,554,849 B1 | 4/2003 | Jones et al. |
| 6,572,648 B1 | 6/2003 | Klumb et al. |
| 6,575,997 B1 | 6/2003 | Palmer et al. |
| 6,585,758 B1 | 7/2003 | Chouinard et al. |
| 6,589,230 B2 | 7/2003 | Gia et al. |
| 6,589,236 B2 | 7/2003 | Wheelock et al. |
| 6,592,607 B1 | 7/2003 | Palmer et al. |
| 6,620,152 B2 | 9/2003 | Guglielmi |
| 6,641,590 B1 | 11/2003 | Palmer et al. |
| 6,645,224 B2 | 11/2003 | Gilson et al. |
| 6,652,548 B2 | 11/2003 | Evans et al. |
| 6,656,214 B1 | 12/2003 | Fogarty et al. |
| 6,660,014 B2 | 12/2003 | Demarais et al. |
| 6,663,650 B2 | 12/2003 | Sepetka et al. |
| 6,673,106 B2 | 1/2004 | Mitelberg et al. |
| 6,679,893 B1 | 1/2004 | Tran |
| 6,692,508 B2 | 2/2004 | Wensel et al. |
| 6,702,782 B2 | 3/2004 | Miller et al. |
| 6,702,843 B1 | 3/2004 | Brown et al. |
| 6,716,238 B2 | 4/2004 | Elliott |
| 6,723,108 B1 | 4/2004 | Jones et al. |
| 6,743,236 B2 | 6/2004 | Barry et al. |
| 6,811,560 B2 | 11/2004 | Jones et al. |
| 6,818,013 B2 | 11/2004 | Mitelberg et al. |
| 6,833,002 B2 | 12/2004 | Stack et al. |
| 6,833,003 B2 | 12/2004 | Jones et al. |
| 6,878,151 B2 | 4/2005 | Carrison et al. |
| 6,887,268 B2 | 5/2005 | Butaric et al. |
| 6,893,413 B2 | 5/2005 | Martin |
| 6,913,612 B2 | 7/2005 | Palmer et al. |
| 6,921,414 B2 | 7/2005 | Klumb et al. |
| 6,945,977 B2 | 9/2005 | Demarais et al. |
| 6,953,468 B2 | 10/2005 | Jones et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 6,974,473 B2 | 12/2005 | Barclay et al. |
| 6,989,020 B2 | 1/2006 | Jones et al. |
| 7,001,422 B2 | 2/2006 | Escamilla et al. |
| 7,004,954 B1 | 2/2006 | Voss et al. |
| 7,004,956 B2 | 2/2006 | Palmer et al. |
| 7,037,331 B2 | 5/2006 | Mitelberg et al. |
| 7,041,116 B2 | 5/2006 | Goto et al. |
| 7,052,500 B2 | 5/2006 | Bashiri et al. |
| 7,058,456 B2 | 6/2006 | Pierce |
| 7,101,380 B2 | 9/2006 | Khachin et al. |
| 7,128,073 B1 | 10/2006 | Van der Burg et al. |
| 7,147,659 B2 | 12/2006 | Jones |
| 7,156,871 B2 | 1/2007 | Jones et al. |
| 7,172,617 B2 | 2/2007 | Colgan et al. |
| 7,179,273 B1 | 2/2007 | Palmer et al. |
| 7,179,276 B2 | 2/2007 | Barry et al. |
| 7,182,774 B2 | 2/2007 | Barry et al. |
| 7,195,648 B2 | 3/2007 | Jones et al. |
| 7,201,769 B2 | 4/2007 | Jones et al. |
| 7,232,432 B2 | 6/2007 | Fulton, III et al. |
| 7,264,628 B2 | 9/2007 | Jones et al. |
| 7,270,674 B2 | 9/2007 | Jones et al. |
| 7,285,126 B2 | 10/2007 | Sepetka et al. |
| 7,294,123 B2 | 11/2007 | Jones et al. |
| 7,306,622 B2 | 12/2007 | Jones et al. |
| 7,309,351 B2 | 12/2007 | Escamilla et al. |
| 7,311,726 B2 | 12/2007 | Mitelberg et al. |
| 7,323,000 B2 | 1/2008 | Monstdt et al. |
| 7,344,550 B2 | 3/2008 | Carrison et al. |
| 7,344,558 B2 | 3/2008 | Lorenzo et al. |
| 7,351,255 B2 | 4/2008 | Andreas |
| 7,357,809 B2 | 4/2008 | Jones et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,481,821 B2 | 1/2009 | Fogarty et al. |
| 7,485,122 B2 | 2/2009 | Teoh |
| 7,510,565 B2 | 3/2009 | Gilson et al. |
| 7,517,352 B2 | 4/2009 | Evans et al. |
| 7,524,319 B2 | 4/2009 | Dubrul |
| 7,534,252 B2 | 5/2009 | Sepetka et al. |
| 7,549,974 B2 | 6/2009 | Nayak |
| 7,553,314 B2 | 6/2009 | Khachin et al. |
| 7,553,321 B2 | 6/2009 | Litzenberg et al. |
| 7,582,101 B2 | 9/2009 | Jones et al. |
| 7,780,694 B2 | 8/2010 | Palmer et al. |
| 7,833,240 B2 | 11/2010 | Okushi et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 8,357,179 B2 | 1/2013 | Grandfield et al. |
| 8,603,014 B2 | 12/2013 | Alleman et al. |
| 8,632,584 B2 | 1/2014 | Henkes et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |

(56) References Cited

U.S. PATENT DOCUMENTS

| | | |
|---|---|---|
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0003801 A1 | 6/2001 | Strecker |
| 2001/0029351 A1 | 10/2001 | Falotico et al. |
| 2001/0039450 A1 | 11/2001 | Pavcnik et al. |
| 2001/0041899 A1 | 11/2001 | Foster |
| 2001/0044649 A1 | 11/2001 | Vallana et al. |
| 2001/0047200 A1 | 11/2001 | White et al. |
| 2001/0053929 A1 | 12/2001 | Vonesh et al. |
| 2002/0016597 A1 | 2/2002 | Dwyer et al. |
| 2002/0111648 A1 | 8/2002 | Kusleika et al. |
| 2002/0188341 A1 | 12/2002 | Elliott |
| 2002/0193868 A1 | 12/2002 | Mitelberg et al. |
| 2003/0120208 A1 | 6/2003 | Houser |
| 2003/0153944 A1 | 8/2003 | Phung et al. |
| 2004/0010308 A1 | 1/2004 | Zafrir-pachter et al. |
| 2004/0059407 A1 | 3/2004 | Escamilla et al. |
| 2004/0068314 A1 | 4/2004 | Jones et al. |
| 2004/0078050 A1 | 4/2004 | Monstadt et al. |
| 2004/0098025 A1 | 5/2004 | Sepetka et al. |
| 2004/0116996 A1 | 6/2004 | Freitag |
| 2005/0021125 A1 | 1/2005 | Stack et al. |
| 2005/0033348 A1 | 2/2005 | Sepetka et al. |
| 2005/0165441 A1 | 7/2005 | Mcguckin et al. |
| 2005/0209678 A1 | 9/2005 | Henkes et al. |
| 2005/0222676 A1 | 10/2005 | Shanley et al. |
| 2006/0085065 A1 | 4/2006 | Krause et al. |
| 2006/0195118 A1 | 8/2006 | Richardson |
| 2006/0224179 A1 | 10/2006 | Kucharczyk et al. |
| 2007/0179513 A1 | 8/2007 | Deutsch |
| 2007/0185501 A1 | 8/2007 | Martin et al. |
| 2007/0198029 A1 | 8/2007 | Martin et al. |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0266542 A1 | 11/2007 | Melsheimer |
| 2007/0288038 A1 | 12/2007 | Bimbo |
| 2008/0039930 A1 | 2/2008 | Jones |
| 2008/0082107 A1 | 4/2008 | Miller et al. |
| 2008/0119888 A1 | 5/2008 | Huffmaster |
| 2008/0183185 A1 | 7/2008 | Miller et al. |
| 2008/0183198 A1 | 7/2008 | Sepetka et al. |
| 2008/0188865 A1 | 8/2008 | Miller et al. |
| 2008/0269774 A1 | 10/2008 | Garcia et al. |
| 2009/0069828 A1 | 3/2009 | Martin et al. |
| 2009/0163851 A1 | 6/2009 | Holloway et al. |
| 2009/0275974 A1 | 11/2009 | Marchand et al. |
| 2010/0174309 A1 | 7/2010 | Fulkerson et al. |
| 2012/0083868 A1 | 4/2012 | Shrivastava et al. |
| 2013/0030461 A1 | 1/2013 | Marks et al. |
| 2013/0281788 A1 | 10/2013 | Garrison |
| 2014/0276074 A1 | 9/2014 | Warner |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 2804058 | 8/1978 |
| DE | 2821048 | 11/1979 |
| DE | 8435489 U1 | 8/1986 |
| DE | 19703482 | 8/1998 |
| EP | 0201466 | 11/1986 |
| EP | 0484468 | 5/1992 |
| EP | 0585326 B1 | 3/1994 |
| EP | 0629125 | 12/1994 |
| EP | 0707830 | 4/1996 |
| EP | 0719522 | 7/1996 |
| EP | 0726745 | 8/1996 |
| EP | 0737450 | 10/1996 |
| EP | 0739606 | 10/1996 |
| EP | 0750886 | 1/1997 |
| EP | 0752236 | 1/1997 |
| EP | 0759730 B1 | 3/1997 |
| EP | 0800790 | 10/1997 |
| EP | 0803230 | 10/1997 |
| EP | 0804904 | 11/1997 |
| EP | 0804905 | 11/1997 |
| EP | 0804906 | 11/1997 |
| EP | 0807410 | 11/1997 |
| EP | 0820729 | 1/1998 |
| EP | 0826341 | 3/1998 |
| EP | 0826342 | 3/1998 |
| EP | 0832606 | 4/1998 |
| EP | 0861634 | 9/1998 |
| EP | 0914803 | 5/1999 |
| EP | 0964659 | 12/1999 |
| EP | 1005837 | 6/2000 |
| EP | 1009295 | 6/2000 |
| EP | 1009296 | 6/2000 |
| EP | 10010840 | 9/2001 |
| EP | 1225844 | 7/2002 |
| EP | 1266639 | 12/2002 |
| EP | 1266640 | 12/2002 |
| EP | 1323385 | 7/2003 |
| EP | 1329196 | 7/2003 |
| EP | 1351626 | 10/2003 |
| EP | 1366720 | 12/2003 |
| EP | 1400219 | 3/2004 |
| EP | 2319575 | 11/2013 |
| FR | 2343488 | 10/1977 |
| GB | 2020557 | 11/1979 |
| JP | 2-95359 A | 4/1990 |
| JP | 02255157 A | 10/1990 |
| JP | 8-033719 A | 2/1996 |
| JP | 2975584 | 11/1999 |
| JP | 2001178830 | 7/2001 |
| JP | 2001190686 | 7/2001 |
| JP | 2003527925 | 9/2003 |
| JP | 2014004219 | 1/2014 |
| JP | 6098939 | 3/2017 |
| JP | 6246004 | 12/2017 |
| JP | 2018118132 | 8/2018 |
| KR | 20180102877 | 9/2018 |
| WO | WO 9617634 | 6/1996 |
| WO | WO 9628116 | 9/1996 |
| WO | WO 97/4711 | 2/1997 |
| WO | WO 9825656 | 10/1998 |
| WO | WO 9855175 | 12/1998 |
| WO | WO 9916382 | 4/1999 |
| WO | WO 9923976 | 5/1999 |
| WO | WO 9925252 | 5/1999 |

(56) References Cited

FOREIGN PATENT DOCUMENTS

| WO | WO 9929264 | 6/1999 |
|---|---|---|
| WO | WO 9944542 | 9/1999 |
| WO | WO 9948429 | 9/1999 |
| WO | WO 9948440 | 9/1999 |
| WO | WO 00/012166 | 3/2000 |
| WO | WO 00/59405 | 10/2000 |
| WO | WO 01/32099 A2 | 5/2001 |
| WO | WO 01/45566 | 6/2001 |
| WO | WO 01/72240 | 10/2001 |
| WO | WO 01/93780 A2 | 12/2001 |
| WO | WO 02/054980 A2 | 7/2002 |
| WO | WO 2004008991 | 1/2004 |
| WO | WO 2008063156 | 5/2008 |
| WO | WO 2009105710 | 8/2009 |
| WO | WO 2015141317 | 9/2015 |
| WO | WO 2017192999 | 11/2017 |
| WO | WO 2018019829 | 2/2018 |
| WO | WO 2018033401 | 2/2018 |
| WO | WO 2018046408 | 3/2018 |
| WO | WO 2018137029 | 8/2018 |
| WO | WO 2018137030 | 8/2018 |
| WO | WO 2018145212 | 8/2018 |
| WO | WO 2018156813 | 8/2018 |
| WO | WO 2018172891 | 9/2018 |
| WO | WO 2018187776 | 10/2018 |

OTHER PUBLICATIONS

Schumacher, H., "Endovascular Mechanical Thrombectomy of an Occluded Superior Division Branch of the Left MCA for Acute Cardioembolic Stroke." Cardiovascular and Interventional Radiology, Jun. 2003 26(3) pp. 305-308.

FIG. 4
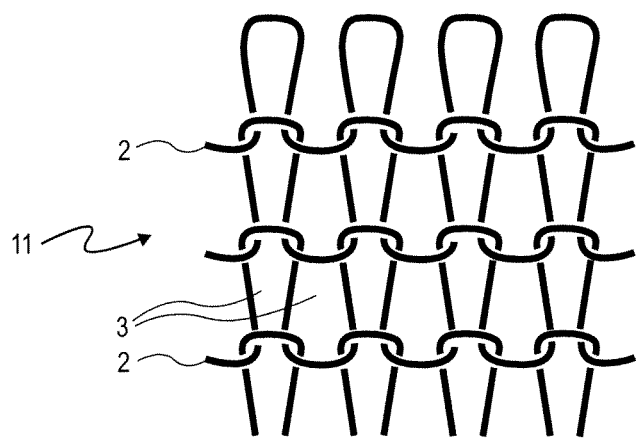
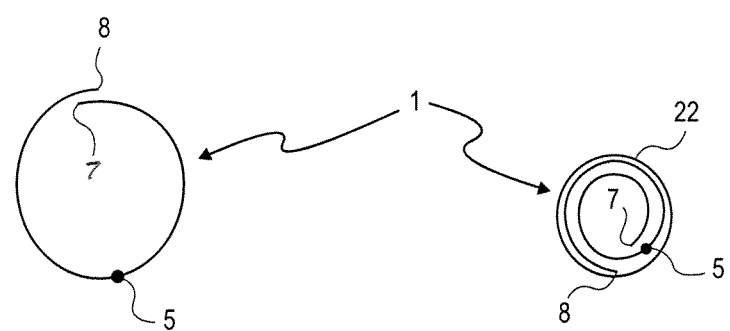
FIG. 6A     FIG. 6B

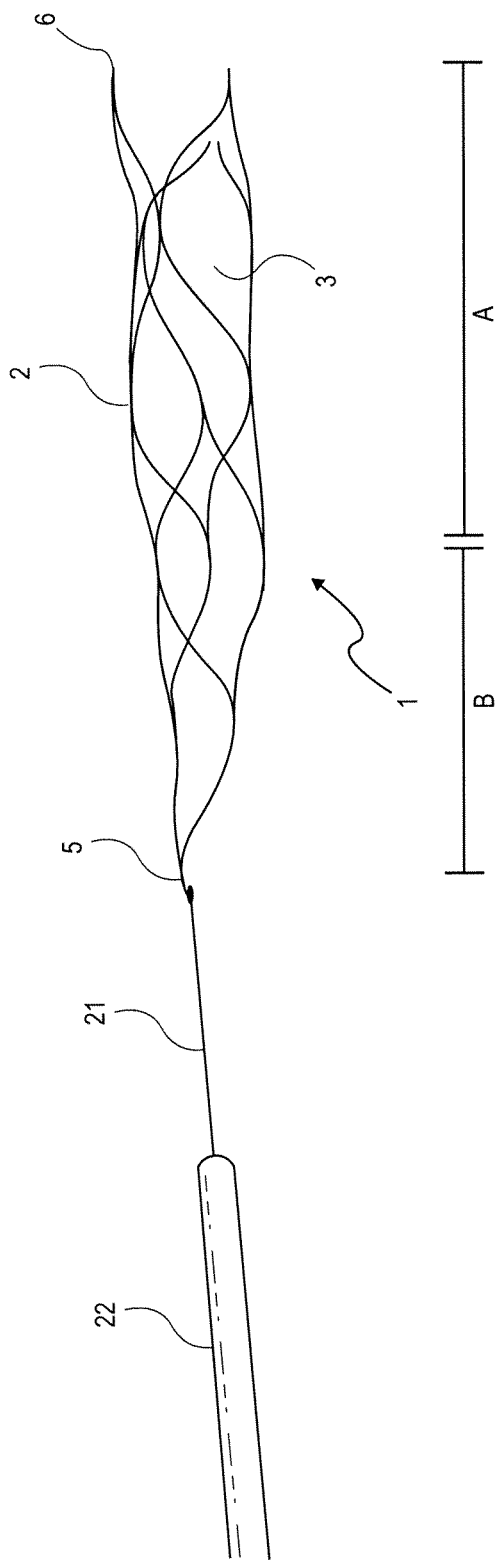

MEDICAL IMPLANT

RELATED APPLICATIONS

This is a continuation of U.S. patent application Ser. No. 14/136,281, filed Dec. 20, 2013, which is a continuation of U.S. patent application Ser. No. 11/935,252, filed Nov. 5, 2007, now U.S. Pat. No. 8,632,584, which is a continuation of U.S. patent application Ser. No. 11/039,066, filed Jan. 19, 2005, now U.S. Pat. No. 7,300,458, which is a continuation of PCT International Application No. PCT/EP2003/007926 filed Jul. 21, 2003, which claims priority of German Patent Application No. 102 33 085.9 filed Jul. 19, 2002, the contents of all of which are incorporated herein by reference.

FIELD OF THE INVENTION

The present invention relates to a medical implant that is preformed in order to assume, at the site of implantation, a superimposed structure and while being implanted is presented in a volume-reduced form. Furthermore, the present invention relates to the application of such an implant as a neuro-stent, its combination with a guide wire as well as a system for the application of such implants when treating aneurysms or other vascular malformations.

BACKGROUND OF THE INVENTION

It is known to treat vasoconstriction (stenoses) with stents (vascular endoprostheses, vessel props) that are inserted into the stenotic area to keep the vessel lumen open. It is further known to use such stents for closing off vessel wall ballooning (aneurysms) or fistulae.

For the foregoing purposes, balloon-dilatable stents are traditionally used. For placement, these stents are crimped over a non-expanded balloon in a non-dilated state, moved to the treatment location by means of a catheter system and then, by expanding the balloon, dilated and thus anchored within the vessel. As there is no need for sophisticated supporting and guiding sheaths when placing balloon-dilatable stents in position, these stents can also be inserted into very fine vessels. It is, however, problematic that on account of their plastic deformability these stents can easily be compressed when external pressure is exerted on them. Another disadvantage is encountered when anchoring such a stent, by applying high pressure, the stent has to be expanded initially beyond the circumferential size it will finally have. Such an expansion beyond the required circumferential size may involve the risk of a vessel injury that may entail the formation of a thrombus.

Further, these traditional balloon-dilatable stents, due to their structure, cannot simply be introduced through an already laid micro-catheter and advanced to the implantation site but have to be arranged in the distal area of a specially designed micro-catheter in order to be moved to the implantation location by means of a so-called pusher. This process calls for a rather sophisticated catheter technology that is difficult to handle. Additionally, a stent, once placed in position, can only be relocated or retrieved with great difficulty, if at all. After a wrongly placed stent has been dilated it can neither be relocated nor removed as a rule.

It is further known to apply self-expanding stents that are made of shape memory materials. These stents possess a braid-like structure and are initially introduced and moved in a collapsed state through a catheter to the destination site where they expand either due to temperature changes (thermo-memory effect) or because the mechanical force exerted by the catheter (super-elasticity) is no longer effective. Such stents, as well, require mechanisms for their introduction that are relatively expensive and space-consuming. The known super-elastic expandable stent requires the use of a supporting and guiding sheath that results in a relatively large catheter size and, what is more, also makes it difficult to introduce such stents through an already laid catheter.

For the introduction into small-lumen intra-cranial vessels, it is furthermore known to use stents made of shape-memory materials that initially are present in the form of an elongated filament. Not until the stent exits the catheter will it assume its tubular structure due to the change in temperature or because of the compression force no longer being exerted by the catheter.

It is known to treat aneurysms and similar diseases by using a stent consisting of two stretched out filaments that due to the mechanical constraint of a strand, are kept, by tension, in the stretched out form until when pushed out of the catheter, said constraint is removed and the strands assume the actual form of a stent. This structure enables the use of stents having shape-memory properties in vessels of very small lumen such as the intra-cranial and cerebral vessel branches.

SUMMARY OF THE INVENTION

The present invention is directed to implants that can be introduced through traditional micro-catheters into small-lumen intra-cranial vessels, that are well placeable and relocatable, that can be moved back into the micro-catheter in case of need, and that are suited to bridge vessel ballooning and fistulae in such a manner that these can be filled with occlusion agents. Furthermore, it is desirable to provide implants capable of adapting to the vessel caliber relatively freely, i.e., not tailored to a specific vessel caliber.

According to the present invention, a medical implant that has the form of a longitudinally open tube with interconnected strings or filaments forming a mesh structure culminating, on one side, in a tapering structure at a connection point is provided.

An implant according to the present invention consists of a flat object that, as a result of its impressed and superimposed structure, assumes the form of a slotted tube or hose with the free edges preferably overlapping. In its volume-reduced form it continues to be present in a curled-up condition, i.e., the diameter of the implant, in a volume-reduced state, is significantly reduced in comparison to that of the superimposed structure. After the implant has been released, it assumes the structure impressed on it and expands to such an extent that the vessel surrounding the implant allows. Such an expansion in the form of an expanding spiral spring shape leads to the implant automatically adapting to the vessel caliber or lumen in such a manner that it can be applied in vessels having different calibers. In the case of narrow vessels, this results in a relatively wide overlap of the two free edges, with wider vessels this overlap is smaller or even a free gap forms which, in the event of vessel branches, is a desirable trait.

In one aspect of the present invention, the implant is a flat or two-dimensional structure that is rolled up to form a longitudinally open object capable of establishing dose contact with the wall of the vessel into which it is introduced.

The strings or filaments taper on one side and culminate in a connection point that permits the implant to be connected to a guide wire to be easily retracted into a catheter in an event of an incorrect placement or inadequate adaptation to the implantation site so that it may be replaced by another implant or reimplanted after the catheter has been repositioned. As a result of its tapering structure, the implant entering the micro-catheter curls up more closely and again assumes its volume-reduced form with the pull force applied to the guide wire and the forces exerted via the catheter rim interacting.

In the catheter itself, the implant is present in its volume-reduced form, resembling rolled up wire netting, Through the action of the guide wire and when thrust forces are applied, an axial compression will be caused, and when released, the superimposed structure assumes a minor longitudinal contraction. Advantageously, the stent according to the present invention exhibits an insignificant longitudinal contraction when released in comparison to dilatable stents.

A connection point of the medical implant situated at the end of the tapered structure serves, at the same time, as a fastening point for the guide wire, either directly or via a connecting elements In the event of a cut or expanded metal foil, this connection point represents the point where the strings of the implant converge. In the case of a mesh-like structure consisting of individual filaments, at least two filaments converge at this connection point and are connected with each other by welding or crimping.

The connection point serves also as a connecting element or part thereof that remains attached to the implant after the guide wire has been detached from the implant. In one embodiment, this connection point is arranged within a platinum spiral or attached to it via a platinum spiral to a connecting element. The spiral may also serve as an X-ray reflecting marker for positioning purposes. In one embodiment the connecting elements are electrolytically corrodible. Such connecting elements enable the implant, after it has been correctly positioned, to be detached from the guide wire by applying electrical energy for brief periods of time, 10 to 60 seconds, for example.

Advantageously, the medical implant according to one embodiment of the invention does not incur a longitudinal contraction when adapting to the vessel. The longitudinally open structure, having a predetermined winding property, has no effect on the longitudinal expansion of the stent. The foil structures have been found to be remarkably true to size under the influence of thrust and tensile forces. The same applies to the warp-knitted structure and the mesh-like structure consisting of individual filaments interconnected by welding.

In an embodiment where the superimposed structure cannot be impressed onto the implants with the help of the warp or weft knitting method or by braiding, material may be put to use that possesses shape-memory properties. For example, such materials consist of alloys containing titanium and nickel which are known by the name of Nitinol, as well as iron and copper based alloys. Shape-memory properties may be based on a stress-induced martensitic transformation or a temperature-induced martensitic transformation or may be the result of a combination of the two.

The implants according to one embodiment of the present invention are also provided with X-ray reflecting markers that enable the positioning and implantation to be monitored. Such markers may have the form of spirals that are arranged proximally, for example, at the connection point of the strings or filaments. The X-ray reflecting markers can also be arranged at the distal end of the implant, in the form of platinum or platinum-iridium elements incorporated in or attached to the mesh structure. The meshes of the implant, according to one embodiment the invention, may, at the distal end, be provided with a lug or end in a lug that accommodates the marker element arranged levelly.

Furthermore, the present invention operates in a combination of the implant with a guide wire that is linked to the distal end of the implant in a manner so as to be detachable. Such detachability is brought about by an element that, under the influence of electrical energy, is capable of corroding. The guide wire can be a known and applied guiding wire of suitable kind for pushing the implant through a catheter to the site of implantation and, should it have been improperly positioned, retract it into the catheter. It is clearly understood that the corrosion point may also be in the area of the guide wire or may be based on an otherwise known mechanical or thermal detachment technique.

The invention also relates to a system to be used for the treatment of aneurysms or other vascular malformations. The system comprises a first micro-catheter, a first guide wire to bring the first microcatheter into position, a second guide wire to move the implant through the first micro-catheter and place it in position and the implant arranged at the distal end of the second guide wire in a way so as to be detachable. Due to the curled up structure of the implant, and as a result of making use of the combination with the guide wire, it is possible, after having placed the first micro-catheter, to remove the first guide wire and introduce and handle the second guide wire which is provided with the implant.

As per one embodiment, the system has additionally been provided with a second micro-catheter to accommodate the second guide wire with the implant in such a way that it is slidable within the second micro-catheter and can be moved through the first micro-catheter to the target site. Coatings of the second micro-catheter that enhance its slidability may facilitate handling.

BRIEF DESCRIPTION OF THE DRAWINGS

The above and further advantages of the invention may be better understood by referring to the following description in conjunction with the accompanying drawings in which:

FIG. 4 is a warp-knitted structure as can be used for an implant according to the invention;

FIG. 5 is a stent according to the present invention together with a guide wire and a catheter;

FIGS. 6A and 6B are schematic representations of an implant according to an embodiment of the present invention shown in its superimposed and in its volume reduced shape;

DETAILED DESCRIPTION

Figure 1:
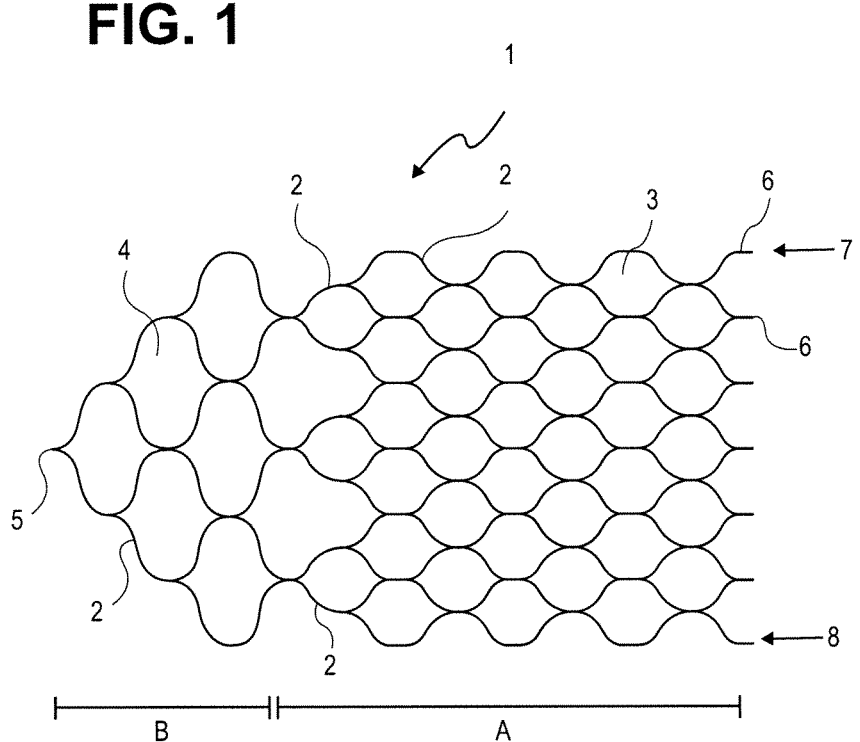
FIG. 1 is an implant according to one embodiment of the present invention having a honeycomb structure.

An implant, according to FIG. 1 consists of a mesh or honeycomb structure that, in one embodiment, comprises a multitude of filaments interconnected by a laser welding technique. The implant can be subdivided into a functional structure A and a tapering proximal structure B, the two structures being distinguishable, inter alia, by a different mesh size. To enable the functional structure A to perform its retaining function, its mesh cells 3 are held relatively narrow so that they lend themselves to the retention of occlusion spirals arranged in an aneurysm. In general, the mesh width is in the range of 0.5 to 4 mm and may vary with in an implant.

In one aspect of the present invention, the implant is a flat or two dimensional structure that is rolled up to form a longitudinally open object capable of establishing close contact with the wall of the vessel into which it is introduced.

In the tapering proximal structure B of the implant, there is provided a wider mesh cell 4 structure which has been optimized towards having a minimum occlusion effect. In the area of the tapering structure 2, the filaments have a greater thickness and/or width to be able to better transfer to the functional structure A the thrust and tensile forces of the guide wire exerted at a connection point 5 when the implant 1 is introduced and placed in position. In the area of the tapering structure it is normally not necessary to provide support for, and coverage of, the vessel wall, but on the other hand requirements as to tensile and thrust strength increase. The filament thickness in the functional structure A generally ranges between 0.02 and 0.070 mm, and in proximal structure part B, the filament thickness is greater than 0.076 mm.

The proximal structure forms an angle from 45° to 120° at the connection point 5, in particular an angle of about 90°. The filament thickness (or string width) is the same as the mesh size and its shape may vary over a great range to suit varying requirements as to stability, flexibility and the like. It is understood that the proximal structure B, as well, contacts the vessel wall and thus does not interfere with the flow of blood within the vessel.

At a distal end, the filaments 2 end in a series of tails 6 that are of suitable kind to carry platinum markers that facilitate the positioning of the implant.

The implant 1 is curled up in such a way that edges 7 and 8, forming first and second lateral edges, are at least closely positioned to each other and may overlap in the area of the edges. In this volume-reduced form, the implant 1, similar to a wire mesh roll, has curled up in a coiled configuration to such an extent that the roll so formed can be introduced into a micro-catheter and moved within the catheter. Having been released from the micro-catheter, the curled-up structure springs open and attempts to assume the superimposed structure previously impressed on it and in doing so closely leans to the inner wall of the vessel to be treated, thus superficially covering a fistula, vessel branch or aneurysm that exists in that location. In this case the extent of the "curl up" is governed by the vessel volume. In narrower vessels a greater overlap of the edges 7 and 8 of the implant 1 will occur whereas in wider vessels the overlap will be smaller or even "underlap," will be encountered, and due care must be exercised to make sure the implant still exhibits a residual tension.

Suitable materials that can be employed in the device include alloys having shape-memory properties. The finished product is subjected to a tempering treatment at temperatures customarily applied to the material so that the impressed structure is permanently established.

The implant has a mesh-like structure consisting of strings or filaments connected with each other. Strings occur if the implant comprises cut structures as, for example, are frequently put to use in coronary stents, a mesh-like structure consisting of filaments is found if the implants are present in the form of mats having knitted or braided structures or in the form of individual filaments that are welded to one another.

Figure 2:
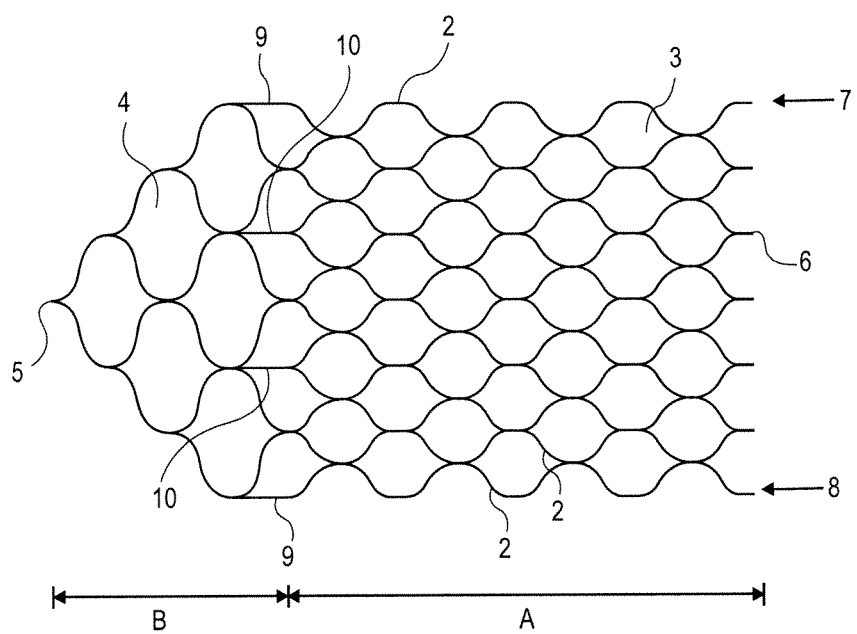
FIG. 2 is another embodiment of a stent according to the present invention having a honeycomb structure.

FIG. 2 shows another embodiment of a stent 1 according to the invention having the above described honeycomb structure where the tapering proximal structure B is connected with the functional structure part A by additional filaments 9 in a peripheral area 10 as well as in the central area. The additional filaments 9 and 10 bring about a more uniform transmission of the tensile and thrust forces from the proximal structure B to the functional structure A. As a result, the tensile forces can be better transmitted, especially if the stent might have to be repositioned by having to be retracted into the microcatheter. The additional filaments 9, 10 facilitate the renewed curling up of the stent. Similarly, the transmission of thrust forces occurring when the stent is moved out and placed in position is facilitated so that the stent can be gently applied.

Figure 3:
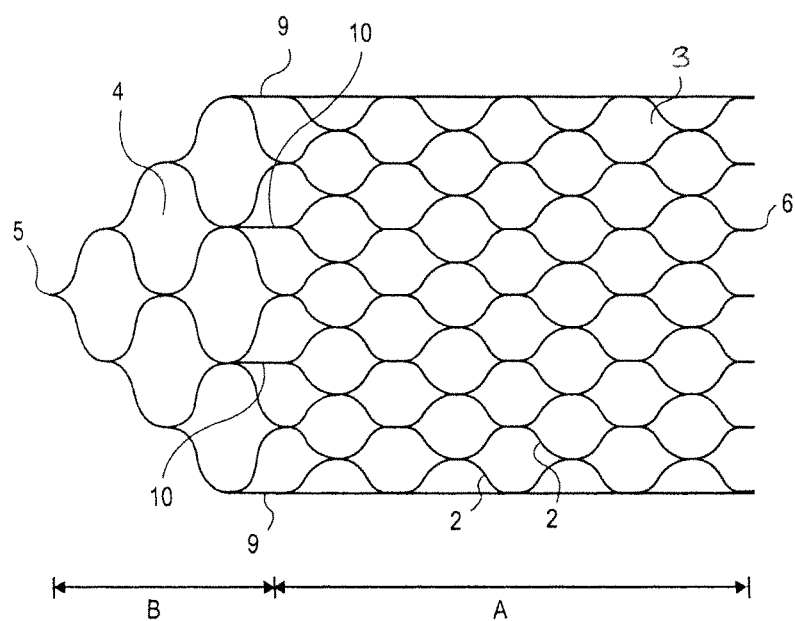
FIG. 3 is a third embodiment of a stent according to the present invention having a honeycomb structure.

FIG. 3 shows another embodiment of a stent 1 according to the invention having a honeycomb structure with the edges 7 and 8 being formed of straight filaments 9. According to this embodiment, the thrust or pressure exerted by the guide wire at the connection point 5 is directly transmitted to the edges 7 and 8 of the functional structure part A which further increases the effect described with reference to FIG. 2.

The embodiment as per FIG. 3, similar to those depicted in FIGS. 1 and 2, may be based on a cut foil, i.e., the individual filaments 2, 9 and 10 are substituted by individual strings being the remaining elements of a foil processed with the help of a cutting technique. Laser cutting techniques for the production of stents having a tubular structure are known. The processing of a foil for the production of a pattern suitable for a stent is performed analogously. The impression of the superimposed structure is carried out in the same way as is used for the filament design. In one embodiment, expanded metal foil may be used with the respective string widths being of the same magnitude. In one embodiment, it is envisioned to subsequently smooth the foil to make sure all strings are arranged on the same plane. The thickness of the foil usually ranges between 0.02 and 0.2 mm. Foils of greater thickness also permit the stent to be used in other fields of application, for example, as coronary stents or in other regions of the body including, for instance, the bile duct or ureter.

Foils worked with the help of a cutting technique are finished by electrochemical means to eliminate burrs and other irregularities to achieve a smooth surface and round edges. One of ordinary skill in the art will understand these electrochemical processes as these processes already are in use in medical technology, in this context, it is to be noted that the stents according to the invention that are based on a two-dimensional geometry and on which a three-dimensional structure is impressed subsequently can be manufactured and processed more easily than the conventional "tubular" stents that already during manufacture, have a three-dimensional structure and necessitate sophisticated and costly working processes and equipment.

As pointed out above, the mesh structure of the implant according to the invention may consist of a braiding of individual filaments. Such a knitted structure is shown in FIG. 4 where the individual filaments 2 are interwoven in the form of a "single jersey fabric" having individual loops 3 forming a mesh-like structure 11. Single jersey goods of this type are produced in a known manner from a row of needles. The single jersey goods have two fabric sides of different appearance, i.e., the right and left side of the stitches. A single jersey fabric material features minor flexibility in a transverse direction and is very light.

Filaments consisting of a braid of individual strands and formed into a rope can also be employed. Braids comprising twelve to fourteen strands having a total thickness of 0.02 mm can be used. Platinum, platinum alloys, gold and stainless steel can be used as materials for the filaments. Generally speaking, all permanent implant materials known in medical technology can be employed that satisfy the relevant requirements.

In one embodiment, it is advantageous to have the fabric rims of such a knitted structure curling up as is known, for example, from the so-called "Fluse" fabric, a German term, which is of benefit with respect to the superimposed structure and application dealt with here. In this case, the superimposed structure can be impressed by means of the knitting process. However, the use of shape-memory alloys in this case as we is feasible and useful.

For the production of such knitted structures, known knitting processes and techniques can be employed. However, since the implants according to the invention are of extremely small size—for example, a size of 2 by 1 cm—it has turned out to be beneficial to produce the implants in the framework of a conventional warp or weft knitting fabric of textile, non-metallic filaments, for example, in the form of a nm consisting of the respective metallic filaments from which the weft or warp knitting fabric either starts out or that extends from such a fabric. The arrangement of the metallic part of the weft or warp knitting fabric at the rim achieves the aforementioned curling effect. The non-metallic portions of the knitted fabric are finally removed by incineration, chemical destruction or dissolution using suitable solvents, FIG. 5 shows a combination of a guide wire 21 with the implant 1 attached to it that consists of filaments 2 connected to each other by welding, The distal ends 6 and the connection point 5 where the filaments of the implant converge in a tapering structure and that simultaneously represents the joining iodation with guide wire 21 are shown. The guide wire 21 is introduced into a micro-catheter 22 which is of customary make.

Shifting the guide wire 21 within the catheter 22 will cause the implant 1 to be pushed out of or drawn into the catheter. Upon the stent being pushed out of the micro-catheter the mesh-like structure attempts to assume the superimposed shape impressed on it, and when being drawn in, the mesh structure folds back into the micro-catheter adapting to the space available inside, As a result of the stiffness of its mesh structure, the implant can be moved to and fro virtually without restriction is the guide wire 21 until it has been optimally positioned within the vessel system.

As mentioned earlier, customary micro-catheters can be used. One advantage of the implant according to the invention and of the combination of implant and guide wire according to the invention is, however, that after having placed the micro-catheter in position with a customary guide wireimarker system, the combination of guide wire 21 and implant 1 according to the invention can be introduced into the micro-catheter, moved through it towards the implantation site and then moved out and applied in that position. Alternatively, it will be possible to have a second micro-catheter of smaller caliber accommodate guide wire 21 and implant 1 and with this second micro-catheter within the firstly positioned micro-catheter shift them to the implantation site. In any case, the implant can be easily guided in both directions.

FIG. 6 shows a schematic representation of an implant according to the invention in its superimposed or volume-expanded shape and in its volume-reduced shape. In its expanded shape, as illustrated in FIG. 6a, the implant 1 forms a ring-shaped structure with slightly overlapping edges land 8. In FIG. 6a the implant 1 is viewed from its proximal end as a top view with the connection point 5 being approximately positioned opposite to the edges 7 and 8. In the combination according to the invention, the guide wire 21 is affixed at the connection point 5.

FIG. 6b shows the same implant in its volume-reduced form as it is arranged, for example, in a micro-catheter in a curled up condition. In the case illustrated there is a total of two windings of the curled-up implant 1 with the connection point 5 being located at the proximal side and the two lateral edges 7 and 8 being the starting and final points of the roll or spiral. The structure is held in its volume-reduced form by the micro-catheter 22 and when the implant 1 is pushed out of the micro-catheter 22 it springs into its expanded shape, as illustrated by FIG. 6a, similar to a spiral spring.

Figure 7A:
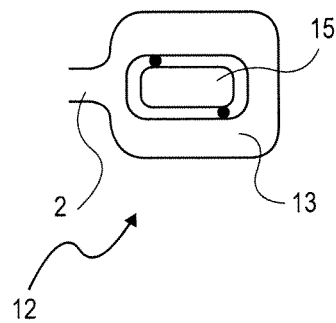
FIGS. 7A and 7B show a marker element as can be used in the system according to the present invention.
Figure 7B:
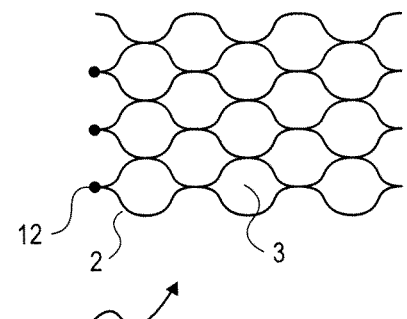

FIG. 7a shows a marker element 12 suitable for the implant according to the invention with the marker element 12 being capable of being arranged at the distal end of the implant 1. The marker element 12 consists of a lug 13 provided with a small marker plate 15 levelly arranged inside it, i.e., flush with the plane of the implant without any projecting elements. The plate 15 is made of an X-ray reflecting material, for example, platinum or platinum-iridium. The marker plate 15 may be connected to the surrounding implant structure by known laser welding techniques. As shown in FIG. 7b, the marker elements 12 are arranged at the distal end of the implant 1.

Figure 8A:
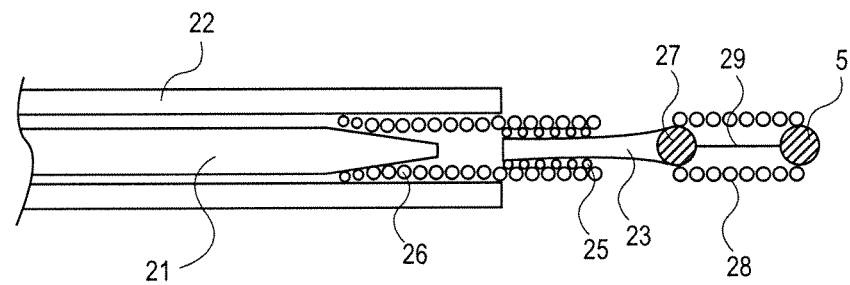
FIGS. 8A and 8B are schematic representations of two detachment locations by which the implant, according to the present invention, can be detachably linked to a guide wire.
Figure 8B:
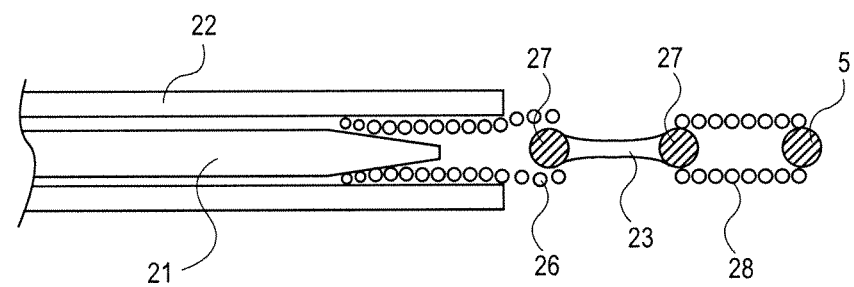

FIGS. 8a and 8b are representations, respectively, of two variations of a separating arrangement by which the implant 1 according to the invention is detachably connected to a guide wire 21. In each case, a separating arrangement consists of a dumb-bell shaped element 23 that dissolves under the influence of electrical energy when in contact with an electrolyte. At the proximal (guide-wire side) end of the dumb-bell shaped separating element 23, as per FIG. 8a, a spiral structure 25 is located that interacts with a strengthening spiral 26 of the guide wire 21. At the distal end, a ball-shaped element 27 is arranged that with the help of a laser welding technique, is connected to a platinum spiral 28 which, in turn, is linked with the connection point 5 situated at the proximal end of the implant 1. The platinum spiral 28 also serves as an X-ray reflecting proximal marker of the implant 1.

To strengthen the joint between the ball-shaped element 27 and the connection point 5, a reinforcement wire 29 may be provided. Alternatively, the platinum spiral 28 may also be designed in such a manner that it withstands the tensile and thrust forces imposed on it.

The separating element 23 can include a steel material that is susceptible to corrosion in an electrolyte under the influence of electrical energy. To accelerate corrosion and shorten the separating time span, a structural or chemical weakening of the dumb-bell shaped element 23 may be beneficial, for example, by applying grinding methods or thermal treatment.

Generally, the portion of the dumb-bell 23 accessible to the electrolyte has a length of 0.1 to 0.5 mm, particularly 0.3 mm.

The spiral structure 25 is secured via welding both to the dumb-bell shaped element 23 and the reinforcement spiral 26 of the guide wire 21. The guide wire 21 itself is slidably accommodated within the micro-catheter 22.

FIG. 8b shows a second embodiment that differs from the one described with respect to FIG. 8a, in that the dumb-bell shaped element 23 has a ball-shaped element 27 at each end. The ball shaped elements 27 are connected distally to the connection point 5 of the implant 1 and proximally to the guide wire 21 via spirals 28, 26, respectively.

It is of course also provided that other separating principles may be applied, for example, those that are based on mechanical principles or melting off plastic connecting elements.

Although various exemplary embodiments of the present invention have been disclosed, it will be apparent to those skilled in the art that changes and modifications can be made which will achieve some of the advantages of the invention without departing from the spirit and scope of the invention. It will be apparent to those reasonably skilled in the art that other components performing the same functions may be suitably substituted.

The invention claimed is:

1. A medical device comprising:
a guide wire;
a longitudinally open laser-cut structure consisting of:
a first portion consisting of a laser-cut mesh of individual filaments defining a first plurality of cells, and having a distal end and a proximal end, the first portion forming a longitudinal tube, the distal end of the first portion being open; and
a second portion consisting of a laser-cut mesh of individual filaments defining a second plurality of cells, and having a distal end and a proximal end, the second portion located proximal to the first portion, and the distal end of the second portion attached to the proximal end of the first portion,
wherein each of the cells of the first portion are smaller than each of the cells of the second portion; and
a connection between the guide wire and the longitudinally open structure at the proximal end of the second portion,
wherein the proximal end of the second portion is open and tapers toward the connection, and the guide wire extends proximally of the proximal end of the second portion and is configured to introduce the first and second portions through a microcatheter.

2. The medical device of claim 1, wherein the longitudinal tube is self-expandable due to shape memory of the first portion.

3. The medical device of claim 1, wherein the cells of the first portion are smaller, in a latitudinal direction of the medical device, than the cells of the second portion.

4. The medical device of claim 1, wherein at least one of the first or second portions comprises Nitinol.

5. The medical device of claim 1, wherein the device is retractable proximally by the guide wire into a catheter to collapse the longitudinal tube.

6. The medical device of claim 1, wherein the guide wire is detachably coupled to the second portion.

7. The medical device of claim 6, wherein the connection comprises an electrolytically corrodible element.

8. The medical device of claim 1, wherein the guide wire comprises a spiral.

9. The medical device of claim 1, wherein the connection comprises a spiral.

10. The medical device of claim 1, wherein the connection is X-ray reflecting.

11. The medical device of claim 1, further comprising a plurality of markers attached to the longitudinally open structure.

12. A medical device comprising:
a longitudinally open structure consisting of:
a first portion consisting of a laser-cut mesh of individual filaments defining a first plurality of cells, and having a distal end and a proximal end, the first portion forming a longitudinal tube, the distal end of the first portion being open; and
a second portion consisting of a laser-cut mesh of individual filaments defining a second plurality of cells, and having a distal end and a proximal end, the second portion located proximal to the first portion, and the distal end of the second portion attached to the proximal end of the first portion, the proximal end of the second portion tapering toward a connection point, wherein the cells of the first portion are smaller than the cells of the second portion,
wherein a first lateral edge extends from the distal end of the first portion to the proximal end of the second portion and a second lateral edge extends from the distal end of the first portion to the proximal end of the second portion, the first and second lateral edges being overlapped by a first amount in a coiled configuration when the medical device is in a volume-reduced form, the first and second lateral edges being overlapped by a second amount less than the first amount when the medical device is in a volume-expanded form; and
a guide wire coupled to the proximal end of the second portion at the connection point, the guide wire extending proximally from the connection point and configured to introduce the longitudinally open structure through a microcatheter.

13. The medical device of claim 12, wherein the longitudinal tube is self-expandable due to shape memory of the first portion.

14. The medical device of claim 12, wherein at least one of the first or second portions comprises Nitinol.

15. The medical device of claim 12, wherein the device is retractable proximally by the guide wire into a catheter to collapse the longitudinal tube.

16. The medical device of claim 12, wherein the guide wire is detachably coupled to the second portion.

17. The medical device of claim 16, wherein the connection point comprises an electrolytically corrodible element.

18. The medical device of claim 12, wherein the guide wire comprises a spiral.

19. The medical device of claim 12, wherein the connection point comprises a spiral.

20. The medical device of claim 12, wherein the connection point is X-ray reflecting.

21. The medical device of claim 12, further comprising a plurality of markers attached to the longitudinally open structure.

* * * * *

UNITED STATES PATENT AND TRADEMARK OFFICE
CERTIFICATE OF CORRECTION

PATENT NO. : 11,426,293 B2
APPLICATION NO. : 16/420814
DATED : August 30, 2022
INVENTOR(S) : Henkes et al.

It is certified that error appears in the above-identified patent and that said Letters Patent is hereby corrected as shown below:

On the Title Page

Item (54), in Column 1, in "Title", Line 1, delete "MEDICAL IMPLANT" and insert -- MEDICAL IMPLANT AND METHOD OF USE --, therefor.

In the Specification

In Column 1, Line 1, delete "MEDICAL IMPLANT" and insert -- MEDICAL IMPLANT AND METHOD OF USE --, therefor.

Signed and Sealed this
Eleventh Day of October, 2022

Katherine Kelly Vidal
*Director of the United States Patent and Trademark Office*